(12) United States Patent
Ling et al.

(10) Patent No.: US 11,976,139 B2
(45) Date of Patent: May 7, 2024

(54) SODIUM HYALURONATE WITH FULL MOLECULAR WEIGHT DISTRIBUTION (MWD), AND PREPARATION METHOD AND USE THEREOF

(71) Applicants: MEYER BIO-MEDICINE CO., LTD., Jinan (CN); SHANDONG MEIMAO PHARMACEUTICAL CO., LTD., Jinan (CN); SHANDONG GUANTIANXIA BIOTECHNOLOGY CO., LTD., Linyi (CN)

(72) Inventors: Peixue Ling, Jinan (CN); Huarong Shao, Jinan (CN); Qingkai Zeng, Jinan (CN)

(73) Assignees: MEYER BIO-MEDICINE CO., LTD., Jinan (CN); SHANDONG MEIMAO PHARMACEUTICAL CO., LTD., Jinan (CN); SHANDONG GUANTIANXIA BIOTECHNOLOGY CO., LTD., Linyi (CN)

( * ) Notice: Subject to any disclaimer, the term of this patent is extended or adjusted under 35 U.S.C. 154(b) by 0 days.

(21) Appl. No.: 18/038,777

(22) PCT Filed: Jul. 31, 2022

(86) PCT No.: PCT/CN2022/109329
§ 371 (c)(1),
(2) Date: May 25, 2023

(87) PCT Pub. No.: WO2023/006108
PCT Pub. Date: Feb. 2, 2023

(65) Prior Publication Data
US 2024/0002551 A1 Jan. 4, 2024

(30) Foreign Application Priority Data

Jul. 30, 2021 (CN) .......................... 202110874694.1

(51) Int. Cl.
| | | |
|---|---|---|
| *C08B 37/08* | (2006.01) | |
| *A61K 8/73* | (2006.01) | |
| *A61K 31/728* | (2006.01) | |
| *A61P 17/02* | (2006.01) | |
| *A61P 29/00* | (2006.01) | |
| *A61Q 19/00* | (2006.01) | |
| *B01D 15/00* | (2006.01) | |
| *B01D 61/02* | (2006.01) | |
| *B01D 61/04* | (2006.01) | |
| *B01D 69/02* | (2006.01) | |

(52) U.S. Cl.
CPC .......... *C08B 37/0072* (2013.01); *A61K 8/735* (2013.01); *A61K 31/728* (2013.01); *A61P 17/02* (2018.01); *A61P 29/00* (2018.01); *A61Q 19/00* (2013.01); *B01D 15/00* (2013.01); *B01D 61/027* (2013.01); *B01D 61/04* (2013.01); *B01D 69/02* (2013.01); *B01D 2311/04* (2013.01); *B01D 2325/34* (2013.01)

(58) Field of Classification Search
CPC .. C08B 37/0072; A61K 31/728; B01D 43/00; B01D 61/02; B01D 61/027; B01D 61/04; B01D 69/02
See application file for complete search history.

(56) References Cited

U.S. PATENT DOCUMENTS

| | | | |
|---|---|---|---|
| 6,020,484 A | 2/2000 | Callegaro et al. | |
| 2013/0165404 A1* | 6/2013 | De Rosa ................... | C08L 5/16 514/54 |

FOREIGN PATENT DOCUMENTS

| | | |
|---|---|---|
| CN | 104059166 A | 9/2014 |
| CN | 108484796 A | 9/2018 |
| CN | 110423291 A | 11/2019 |
| CN | 112076127 A | 12/2020 |
| CN | 112553273 A | 3/2021 |

(Continued)

OTHER PUBLICATIONS

D'Agastino, A. et al "In vitro analysis of the effects on wound healing . . . " BMC Cell Biol., vol. 16, No. 19, pp. 1-15. (Year: 2015).*
Kakehi, K. et al "Hyaluronic acid: separation and biological implications" J. Chromatogr. B, vol. 797, pp. 347-355. (Year: 2003).*
Stern, R. et al "The many ways to cleave hyaluronan" Biotechnol. Adv., vol. 25, pp. 537-557. (Year: 2007).*

(Continued)

*Primary Examiner* — Leigh C Maier
(74) *Attorney, Agent, or Firm* — Bayramoglu Law Offices LLC

(57) ABSTRACT

A preparation method of sodium hyaluronate with a full molecular weight distribution (MWD) is provided, including: step 1): spraying hydrogen peroxide on a sodium hyaluronate solid raw material, and conducting an ultraviolet (UV) irradiation treatment; step 2): dissolving a sodium hyaluronate degradation material in water, and adjusting a pH to higher than 7.0; step 3): subjecting a sodium hyaluronate alkaline solution to an ultrasonic treatment; step 4): preparing the sodium hyaluronate solid raw material into a sodium hyaluronate solution with a concentration of 0.1% to 1% (w/v), and thoroughly mixing the sodium hyaluronate solution in an addition proportion of 20% to 60% (v/v) with the sodium hyaluronate alkaline solution obtained after the ultrasonic treatment; and step 5): subjecting a resulting mixed solution to an adsorption treatment with diatomaceous earth and activated carbon, filtering for concentration, and drying a resulting concentrate to obtain the sodium hyaluronate with a full MWD.

13 Claims, No Drawings

(56) References Cited

FOREIGN PATENT DOCUMENTS

| CN | 112920289 A | 6/2021 |
|---|---|---|
| CN | 113512134 A | 10/2021 |

OTHER PUBLICATIONS

EPO machine translation of CN 112920289A. (Year: 2021).*
Zhang Wen-Qiang, et al., Preparation of low-molecular-weight hyaluronan using ultrasonic degradation, Journal of Clinical Rehabilitative Tissue Engineering Research, 2009, pp. 4883-4885, vol. 13, No. 25.
Hongyue Chen, et al., Efficient Degradation of High-Molecular-Weight Hyaluronic Acid by a Combination of Ultrasound, Hydrogen Peroxide, and Copper Ion, Molecules, 2019, pp. 1-12, vol. 24, No. 617.

* cited by examiner

SODIUM HYALURONATE WITH FULL MOLECULAR WEIGHT DISTRIBUTION (MWD), AND PREPARATION METHOD AND USE THEREOF

CROSS REFERENCE TO THE RELATED APPLICATIONS

This application is the national phase entry of International Application No. PCT/CN2022/109329, filed on Jul. 31, 2022, which is based upon and claims priority to Chinese Patent Application No. 202110874694.1, filed on Jul. 30, 2021, the entire contents of which are incorporated herein by reference.

TECHNICAL FIELD

The present application relates to the technical field of biological materials, and specifically relates to sodium hyaluronate with a full molecular weight distribution (MWD), and a preparation method and use thereof.

BACKGROUND

Hyaluronic acid (HA) is a linear polysaccharide obtained by linking D-glucuronic acid and N-acetyl-D-glucosamine, and has a molecular weight ranging from hundreds of thousands of daltons to millions of daltons. HA is widely distributed in animal tissues, with the highest content being found in human skin, umbilical cords, vitreous bodies, and synovial fluids, and is also widely distributed in plants and microorganisms. In nature, HA has a consistent structure, and does not have racial diversity or immunogenicity.

At a high HA concentration (1%), HA molecules exist in the form of a network with high viscoelasticity. An aqueous solution of HA is a viscoelastic fluid and can be filled in a space between a cell and a collagen fiber and cover some epidermal tissues which mainly plays the role of protecting and lubricating cells and adjusting the movement of the cell on the elastic matrix. HA in skin can lock in moisture to make the skin smooth and delicate and maintain the skin elasticity. HA in human synovial fluids can lubricate joints, isolate the stimulation of harmful signal factors, and protect the functions of joint cartilages. HA in vitreous bodies plays a role in supporting ocular chambers, protecting retinas, and brightening eyes. HA is an ideal natural moisturizing factor (NMF) recognized internationally and can be used in various cosmetics for moisturizing. After being orally administered and absorbed, HA can participate in the synthesis of HA in the body, which is then distributed in human skin, joint cavities, and vitreous bodies, can supplement HA in synovial fluids, and can increase skin elasticity.

HA mostly exhibits in the form of sodium hyaluronate in the production and application, and different types of sodium hyaluronate vary greatly in efficacy. For example, sodium hyaluronate with a high molecular weight (higher than 500,000 Da) has a prominent mucosal protection effect, and sodium hyaluronate with a low molecular weight (10,000 Da to 500,000 Da) and sodium oligomeric hyaluronate with a low molecular weight (less than 10,000 Da) have excellent advantages in skin penetration capacity and oral absorption capacity. Currently, HA products are mainly HA products with a single MWD, which have a narrow MWD and varying qualities. Therefore, in the existing methods, sodium hyaluronate products of different molecular weight ranges need to be mixed to obtain sodium hyaluronate with a wide MWD. However, because sodium hyaluronate products with different molecular weights vary greatly in viscosity and other properties, it is difficult to guarantee the uniformity of a product obtained after direct mixing. Some physical, chemical, or biological sodium hyaluronate degradation methods are also provided in the prior art. However, sodium hyaluronate obtained after a treatment by the existing degradation method has a non-uniform MWD and poor stability, and it is difficult to further improve a quality of the sodium hyaluronate product.

SUMMARY

In order to solve the above problems, the present disclosure is intended to provide high-quality sodium hyaluronate with excellent uniformity, high stability, and a full MWD, and a preparation method and use thereof.

In an aspect, the present application provides a preparation method of sodium hyaluronate with a full MWD, including:

step 1): spraying hydrogen peroxide on a sodium hyaluronate solid raw material, and conducting a UV irradiation treatment to obtain a sodium hyaluronate degradation material;

step 2): dissolving the sodium hyaluronate degradation material in water, and adjusting a pH with a NaOH solution to higher than 7.0 to obtain a sodium hyaluronate alkaline solution;

step 3): subjecting the sodium hyaluronate alkaline solution to an ultrasonic treatment;

step 4): preparing the sodium hyaluronate solid raw material into a sodium hyaluronate solution with a concentration of 0.1% to 1% (w/v), and thoroughly mixing the sodium hyaluronate solution in an addition proportion of 20% to 60% (v/v) with the sodium hyaluronate alkaline solution obtained after the ultrasonic treatment in step 3); and step 5): subjecting a resulting mixed solution to an adsorption treatment with diatomaceous earth and activated carbon, filtering a resulting solution through a nanofiltration membrane for concentration, and drying a resulting concentrate to obtain the sodium hyaluronate with a full MWD.

Further, in step 1), 50 mL to 100 mL of hydrogen peroxide with a mass concentration of 1% to 5% is sprayed on each kilogram of the sodium hyaluronate solid raw material; and the UV irradiation treatment is conducted for 50 min to 70 min at a dose of 300 $\mu W/cm^2$ to 1,500 $\mu W/cm^2$.

It should be understood that the dose of the UV irradiation in the present application refers to a luminous flux of UV light received per unit area. Optionally, the UV irradiation refers to irradiation under a UV lamp with an irradiation wavelength of 200 nm to 400 nm and preferably 220 nm to 320 nm.

Further, the sodium hyaluronate solid raw material has a molecular weight of 1,000,000 Da to 2,000,000 Da.

It should be understood that the molecular weight of the sodium hyaluronate in the present application refers to a weight-average molecular weight.

Further, the sodium hyaluronate solid raw material is one or more selected from the group consisting of cosmetic grade sodium hyaluronate, food grade sodium hyaluronate, and pharmaceutical grade sodium hyaluronate.

Further, in step 2), a concentration of the sodium hyaluronate degradation material in water is 1% to 10% (w/v); and/or
the pH is adjusted with the NaOH solution to 10 to 12.

Further, in step 3), the ultrasonic treatment is conducted for 15 min to 180 min at a frequency of 10 kHz to 100 kHz.

Further, in step 5), an adsorption treatment with the diatomaceous earth includes: adding the diatomaceous earth at a mass 0.1% to 1% (w/v) of a mass of the sodium hyaluronate alkaline solution, stirring a resulting mixture at 45° C. to 80° C. to allow adsorption for 30 min to 60 min, and filtering; and/or an adsorption treatment with the activated carbon includes: adjusting a pH with a dilute acid solution to 6 to 7, adding the activated carbon at a mass 0.1% to 1% (w/v) of the mass of the sodium hyaluronate alkaline solution, stirring a resulting mixture at 45° C. to 80° C. to allow adsorption for 30 min to 60 min, and filtering, where preferably, the dilute acid solution is one or more selected from the group consisting of a dilute hydrochloric acid solution, a dilute sulfuric acid solution, a dilute acetic acid solution, and a dilute hypochlorous acid solution.

Further, in step 5), the nanofiltration membrane has a molecular weight cut-off (MWCO) of 200 Da to 300 Da, and the filtering is conducted at a pressure of 15 bar to 30 bar and a temperature of 30° C. to 50° C.

In another aspect, the present application also provides sodium hyaluronate with a full MWD prepared by the preparation method described above, where the sodium hyaluronate with a full MWD has a weight-average molecular weight of 2,000 Da to 1,500,000 Da and a molecular weight dispersion coefficient Mw/Mn of 5 or more;

preferably, the sodium hyaluronate has an endotoxin content of less than 0.01 EU and a protein content of less than 0.01%; and preferably, the sodium hyaluronate has an OD value of less than 0.01 at 280 nm and an OD value of less than 0.01 at 260 nm.

In another aspect, the present application also provides a use of sodium hyaluronate prepared by the preparation method described above in the preparation of a moisturizer, a lubricant, an anti-inflammatory agent, and/or a cell restorative for a drug, a food, and/or a cosmetic.

Compared with the prior art, the present application has the following beneficial effects:

1. The preparation method provided by the present application can quickly and efficiently prepare sodium hyaluronate with a full MWD, and the prepared sodium hyaluronate has excellent uniformity and high stability, can make full use of efficacy advantages of sodium hyaluronate products with different molecular weights, and has a molecular weight dispersion coefficient Mw/Mn of 5 or more.

2. The preparation method of sodium hyaluronate with a full MWD provided by the present application combines UV irradiation degradation, ultrasound-alkaline hydrolysis, diatomaceous earth filtration, activated carbon adsorption, and nanomembrane filtration, and the prepared sodium hyaluronate has an endotoxin content of less than 0.01 EU, a protein content of less than 0.01%, an OD value of less than 0.01 at 280 nm, an OD value of less than 0.01 at 260 nm, high biocompatibility, and a high quality level, which is conducive to improving the application effects of sodium hyaluronate in skin moisturizing, cytoprotection, and oral administration.

3. In the preparation method of sodium hyaluronate with a full MWD provided by the present application, UV irradiation degradation and ultrasonic degradation are conducted before the filtration of the high-viscosity HA solution, which greatly reduces the difficulty of filtering the high-viscosity solution, improves the preparation efficiency and yield, and improves the efficiency of impurity removal.

4. The preparation method of sodium hyaluronate with a full MWD provided by the present application leads to high-quality sodium hyaluronate with a full MWD, which has superior intelligent moisturizing, anti-inflammatory, and cytoprotective activities.

DETAILED DESCRIPTION OF THE EMBODIMENTS

In order to clearly illustrate the overall conception of the present application, the present application is described in detail below through examples. Those skilled in the art should understand that the following examples are only intended to illustrate the present application, rather than to limit the scope of the present application.

Example 1

In this example, a preparation method of sodium hyaluronate with a full MWD was provided, specifically including the following steps:

Step 1): 1 kg of a food grade sodium hyaluronate raw material with a molecular weight of 1,000,000 Da was taken, 50 mL of 1% hydrogen peroxide was evenly sprayed on a surface of the food grade sodium hyaluronate raw material, and UV irradiation was conducted for 60 min at a dose of 300 µW/cm².

Step 2): A food grade sodium hyaluronate raw material obtained after the UV irradiation was dissolved in water with a concentration of 1% (w/v), and a resulting solution was stirred at room temperature for thorough dissolution.

Step 3): A pH was adjusted with a 2% NaOH solution to 10, and a resulting solution was then subjected to an ultrasonic treatment at 10 kHz for 15 min.

Step 4): A sodium hyaluronate solution with a concentration of 1% (w/v) was prepared using a sodium hyaluronate raw material with a molecular weight of 1,000,000 Da, and then mixed in an addition proportion of 60% (v/v) with the sodium hyaluronate alkaline solution obtained after the ultrasonic treatment.

Step 5): 0.1% diatomaceous earth was added, and a resulting mixture was stirred at 45° C. to allow an adsorption treatment for 30 min and then filtered.

Step 6): A pH was adjusted with a 2% dilute hydrochloric acid solution to 5.0, then 0.1% activated carbon was added, and a resulting mixture was stirred at 45° C. to allow an adsorption treatment for 30 min and then filtered.

Step 7): A nanofiltration membrane system with MWCO of 300 Da was used to concentrate a filtrate at an operating pressure of 15 bar and a temperature of 40° C. to obtain a nanofiltration concentrate, and the nanofiltration concentrate was spray-dried to obtain a high-quality sodium hyaluronate sample with a full MWD.

Example 2

In this example, a preparation method of sodium hyaluronate with a full MWD was provided, specifically including the following steps:

Step 1): 1 kg of a food grade sodium hyaluronate raw material with a molecular weight of 1,200,000 Da was taken, 80 mL of 3% hydrogen peroxide was evenly sprayed on a surface of the food grade sodium hyaluronate raw material, and UV irradiation was conducted for 60 min at a dose of 600 µW/cm².

Step 2): A food grade sodium hyaluronate raw material obtained after the UV irradiation was dissolved in water with a concentration of 3% (w/v), and a resulting solution was stirred at room temperature for thorough dissolution.

Step 3): A pH was adjusted with a 5% NaOH solution to 12, and a resulting solution was then subjected to an ultrasonic treatment at 30 kHz for 30 min.

Step 4): A sodium hyaluronate solution with a concentration of 0.8% (v/v) was prepared using a sodium hyaluronate raw material with a molecular weight of 1,200,000 Da, and then mixed in an addition proportion of 40% with the sodium hyaluronate alkaline solution obtained after the ultrasonic treatment.

Step 5): 0.2% diatomaceous earth was added, and a resulting mixture was stirred at 50° C. to allow an adsorption treatment for 40 min and then filtered.

Step 6): A pH was adjusted with a 2% dilute sulfuric acid solution to 5.0, then 0.3% activated carbon was added, and a resulting mixture was stirred at 50° C. to allow an adsorption treatment for 50 min and then filtered.

Step 7): A nanofiltration membrane system with MWCO of 250 Da was used to concentrate a filtrate at an operating pressure of 20 bar and a temperature of 50° C. to obtain a nanofiltration concentrate, and the nanofiltration concentrate was spray-dried to obtain a high-quality sodium hyaluronate sample with a full MWD.

Example 3

In this example, a preparation method of sodium hyaluronate with a full MWD was provided, specifically including the following steps:

Step 1): 1 kg of a cosmetic grade sodium hyaluronate raw material with a molecular weight of 1,200,000 Da was taken, 80 mL of 5% hydrogen peroxide was evenly sprayed on a surface of the cosmetic grade sodium hyaluronate raw material, and UV irradiation was conducted for 60 min at a dose of 900 μW/cm$^2$.

Step 2): A cosmetic grade sodium hyaluronate raw material obtained after the UV irradiation was dissolved in water with a concentration of 5% (w/v), and a resulting solution was stirred at room temperature for thorough dissolution.

Step 3): A pH was adjusted with a 5% (w/v) NaOH solution to 12, and a resulting solution was then subjected to an ultrasonic treatment at 60 kHz for 60 min.

Step 4): A sodium hyaluronate solution with a concentration of 0.6% (w/v) was prepared using a sodium hyaluronate raw material with a molecular weight of 1,200,000 Da, and then mixed in an addition proportion of 40% (v/v) with the sodium hyaluronate alkaline solution obtained after the ultrasonic treatment.

Step 5): 0.4% diatomaceous earth was added, and a resulting mixture was stirred at 55° C. to allow an adsorption treatment for 40 min and then filtered.

Step 6): A pH was adjusted with a 2% dilute sulfuric acid solution to 5.0, then 0.3% activated carbon was added, and a resulting mixture was stirred at 55° C. to allow an adsorption treatment for 50 min and then filtered.

Step 7): A nanofiltration membrane system with MWCO of 200 Da was used to concentrate a filtrate at an operating pressure of 30 bar and a temperature of 50° C. to obtain a nanofiltration concentrate, and the nanofiltration concentrate was spray-dried to obtain a high-quality sodium hyaluronate sample with a full MWD.

Example 4

In this example, a preparation method of sodium hyaluronate with a full MWD was provided, specifically including the following steps:

Step 1): 1 kg of a cosmetic grade sodium hyaluronate raw material with a molecular weight of 1,400,000 Da was taken, 100 mL of 5% hydrogen peroxide was evenly sprayed on a surface of the cosmetic grade sodium hyaluronate raw material, and UV irradiation was conducted for 60 min at a dose of 1,200 μW/cm$^2$.

Step 2): A cosmetic grade sodium hyaluronate raw material obtained after the UV irradiation was dissolved in water with a concentration of 5% (w/v), and a resulting solution was stirred at room temperature for thorough dissolution.

Step 3): A pH was adjusted with a 6% NaOH solution to 12, and a resulting solution was then subjected to an ultrasonic treatment at 90 kHz for 60 min.

Step 4): A sodium hyaluronate solution with a concentration of 0.3% (w/v) was prepared using a sodium hyaluronate raw material with a molecular weight of 1,400,000 Da, and then mixed in an addition proportion of 30% (v/v) with the sodium hyaluronate alkaline solution obtained after the ultrasonic treatment.

Step 5): 0.6% diatomaceous earth was added, and a resulting mixture was stirred at 55° C. to allow an adsorption treatment for 60 min and then filtered.

Step 6): A pH was adjusted with a 2% dilute sulfuric acid solution to 5.0, then 0.4% activated carbon was added, and a resulting mixture was stirred at 55° C. to allow an adsorption treatment for 60 min and then filtered.

Step 7): A nanofiltration membrane system with MWCO of 200 Da was used to concentrate a filtrate at an operating pressure of 30 bar and a temperature of 50° C. to obtain a nanofiltration concentrate, and the nanofiltration concentrate was spray-dried to obtain a high-quality sodium hyaluronate sample with a full MWD.

Example 5

In this example, a preparation method of sodium hyaluronate with a full MWD was provided, specifically including the following steps:

Step 1): 1 kg of a cosmetic grade sodium hyaluronate raw material with a molecular weight of 1,500,000 Da was taken, 100 mL of 5% hydrogen peroxide was evenly sprayed on a surface of the cosmetic grade sodium hyaluronate raw material, and UV irradiation was conducted for 60 min at a dose of 1,500 μW/cm$^2$.

Step 2): A cosmetic grade sodium hyaluronate raw material obtained after the UV irradiation was dissolved in water with a concentration of 3% (w/v), and a resulting solution was stirred at room temperature for thorough dissolution.

Step 3): A pH was adjusted with a 5% NaOH solution to 12, and a resulting solution was then subjected to an ultrasonic treatment at 90 kHz for 60 min.

Step 4): A sodium hyaluronate solution with a concentration of 0.3% (w/v) was prepared using a sodium hyaluronate raw material with a molecular weight of 1,500,000 Da, and then mixed in an addition proportion of 20% (v/v) with the sodium hyaluronate alkaline solution obtained after the ultrasonic treatment.

Step 5): 0.8% diatomaceous earth was added, and a resulting mixture was stirred at 55° C. to allow an adsorption treatment for 30 min and then filtered.

Step 6): A pH was adjusted with a 2% dilute sulfuric acid solution to 5.0, then 0.6% activated carbon was added, and a resulting mixture was stirred at 55° C. to allow an adsorption treatment for 30 min and then filtered.

Step 7): A nanofiltration membrane system with MWCO of 300 Da was used to concentrate a filtrate at an operating pressure of 30 bar and a temperature of 50° C. to obtain a nanofiltration concentrate, and the nanofiltration concentrate was spray-dried to obtain a high-quality sodium hyaluronate sample with a full MWD.

Example 6

In this example, a preparation method of sodium hyaluronate with a full MWD was provided, specifically including the following steps:

Step 1): 1 kg of a cosmetic grade sodium hyaluronate raw material with a molecular weight of 2,000,000 Da was taken, 100 mL of 5% hydrogen peroxide was evenly sprayed on a surface of the cosmetic grade sodium hyaluronate raw material, and UV irradiation was conducted for 60 min at a dose of 1,500 μW/cm².

Step 2): A cosmetic grade sodium hyaluronate raw material obtained after the UV irradiation was dissolved in water with a concentration of 1% (w/v), and a resulting solution was stirred at room temperature for thorough dissolution.

Step 3): A pH was adjusted with a 5% NaOH solution to 12, and a resulting solution was then subjected to an ultrasonic treatment at 100 kHz for 60 min.

Step 4): A sodium hyaluronate solution with a concentration of 0.1% (w/v) was prepared using a sodium hyaluronate raw material with a molecular weight of 2,000,000 Da, and then mixed in an addition proportion of 30% (v/v) with the sodium hyaluronate alkaline solution obtained after the ultrasonic treatment.

Step 5): 1% diatomaceous earth was added, and a resulting mixture was stirred at 55° C. to allow an adsorption treatment for 50 min and then filtered.

Step 6): A pH was adjusted with a 2% dilute sulfuric acid solution to 5.0, then 1% activated carbon was added, and a resulting mixture was stirred at 55° C. to allow an adsorption treatment for 50 min and then filtered.

Step 7): A nanofiltration membrane system with MWCO of 300 Da was used to concentrate a filtrate at an operating pressure of 30 bar and a temperature of 50° C. to obtain a nanofiltration concentrate, and the nanofiltration concentrate was spray-dried to obtain a high-quality sodium hyaluronate sample with a full MWD.

Comparative Example 1

In this comparative example, the commercially-available sodium hyaluronate No. 1 (cosmetic grade, with a weight-average molecular weight of 1,250,000 Da) was adopted.

Comparative Example 2

In this comparative example, the commercially-available sodium hyaluronate No. 2 (cosmetic grade, with a weight-average molecular weight of 100,000 Da) was adopted.

Comparative Example 3

A preparation method in this comparative example was roughly the same as the preparation method in Example 1, except that, in step 1), only 50 mL of 1% hydrogen peroxide was evenly sprayed without the UV irradiation, and a filtrate obtained after the activated carbon adsorption was not subjected to concentration through filtration with a nanofiltration membrane system.

Comparative Example 4

A preparation method in this comparative example was roughly the same as the preparation method in Example 1, except that, in step 1), only UV irradiation was conducted for 60 min at a dose of 300 μW/cm² without the hydrogen peroxide treatment; and a filtrate obtained after the activated carbon adsorption was not subjected to concentration through filtration with a nanofiltration membrane system.

Comparative Example 5

In this comparative example, sodium hyaluronate with a weight-average molecular weight of 2,000,000 Da, sodium hyaluronate with a weight-average molecular weight of 1,000,000 Da, sodium hyaluronate with a weight-average molecular weight of 300,000 Da, and sodium oligomeric hyaluronate with a weight-average molecular weight of less than 10,000 Da were mixed in a mass ratio of 1:1:1:1 and stirred for 60 min to obtain a sodium hyaluronate sample.

Example 7

The different sodium hyaluronate samples obtained in Examples 1 to 6 and Comparative Examples 3 to 5 each were sampled at different positions. The uniformity and stability were determined, and a viscosity of each of different 1% sodium hyaluronate solutions was determined with a No. 3 rotor of an NDJ-1 rotational viscometer at 25° C. and 60 r/min. Each sample obtained after the preparation was stored at 4° C., and 6 months later, sampling was conducted to determine the viscosity. Results were shown in Table 1. The sodium hyaluronate samples obtained in Examples 1 to 6 each had uniform appearance and excellent stability; the sodium hyaluronate samples obtained in Comparative Examples 3 and 4 each had uniform appearance, but exhibited slightly poor stability, high viscosity, and low filtration efficiency, and thus could hardly be filtered by a nanofiltration membrane system; and the sodium hyaluronate sample obtained in Comparative Example 5 had poor uniformity and poor stability.

TABLE 1

Test results of uniformity and stability of sodium hyaluronate

| Group | Uniformity | Viscosity (mPa · s) | | | | Viscosity after 6 months (mPa · s) | | | |
|---|---|---|---|---|---|---|---|---|---|
| | | Sample 1 | Sample 2 | Sample 3 | RSD | Sample 1 | Sample 2 | Sample 3 | RSD |
| Example 1 | Prominent particle uniformity | 1217.18 | 1248.38 | 1233.79 | 1.27% | 1203.36 | 1204.52 | 1239.98 | 1.71% |
| Example 2 | Prominent particle uniformity | 1141.59 | 1131.88 | 1110.72 | 1.40% | 1129.95 | 1120.49 | 1129.57 | 0.48% |
| Example 3 | Prominent particle uniformity | 1102.53 | 1125.24 | 1113.32 | 1.02% | 1101.98 | 1112.94 | 1111.27 | 0.53% |
| Example 4 | Prominent particle uniformity | 1092.4 | 1088.12 | 1081.75 | 0.49% | 1081.97 | 1087.94 | 1081.82 | 0.32% |
| Example 5 | Prominent particle uniformity | 1068.73 | 1066.28 | 1069.08 | 0.14% | 1048.05 | 1046.85 | 1049.9 | 0.15% |
| Example 6 | Prominent particle uniformity | 1016.21 | 1026.02 | 1027.14 | 0.59% | 1013.71 | 1003.77 | 1025.14 | 1.05% |
| Comparative | Prominent particle uniformity | 2164.72 | 2148.04 | 2102.55 | 1.50% | 2091.68 | 1957.32 | 1933.51 | 4.28% |
| Comparative | Prominent particle uniformity | 1724.85 | 1771.26 | 1816.84 | 2.60% | 1651.81 | 1610.22 | 1647.8 | 1.40% |

TABLE 1-continued

Test results of uniformity and stability of sodium hyaluronate

| Group | Uniformity | Viscosity (mPa · s) | | | | Viscosity after 6 months (mPa · s) | | | |
|---|---|---|---|---|---|---|---|---|---|
| | | Sample 1 | Sample 2 | Sample 3 | RSD | Sample 1 | Sample 2 | Sample 3 | RSD |
| Comparative Example 5 | Slightly poor particle uniformity | 1641.25 | 1537.82 | 1375.85 | 8.81% | 1368.21 | 1396.78 | 1206.81 | 7.74% |

Example 8

The sodium hyaluronate samples obtained in the examples and comparative examples each were subjected to an MWD test, and proportions of sodium hyaluronate molecules with weight-average molecular weights Mw of 2,000 Da to 10,000 Da, 10,000 Da to 300,000 Da, 300,000 Da to 1,000,000 Da, and higher than 1,000,000 Da were shown in Table 2.

TABLE 2

MWD test results of sodium hyaluronate

| Group | 2,000 Da to 10,000 Da | 10,000 Da to 300,000 Da | 300,000 Da to 1,000,000 Da | Higher than 1,000,000 Da | Molecular weight dispersion coefficient Mw/Mn |
|---|---|---|---|---|---|
| Example 1 | 5% | 24% | 26% | 45% | 5.2 |
| Example 2 | 10% | 27% | 35% | 28% | 5.6 |
| Example 3 | 16% | 32% | 30% | 22% | 6.1 |
| Example 4 | 22% | 34% | 25% | 19% | 6.5 |
| Example 5 | 26% | 35% | 25% | 14% | 6.9 |
| Example 6 | 25% | 27% | 30% | 18% | 7.1 |
| Comparative Example 1 | 0 | 6% | 34% | 60% | 1.2 |
| Comparative Example 2 | 32% | 54% | 14% | 0 | 1.7 |
| Comparative Example 3 | 0 | 22% | 46% | 32% | 2.0 |
| Comparative Example 4 | 0 | 26% | 49% | 25% | 2.2 |

It can be seen from the data in Table 2 that, compared with sodium hyaluronate products of obtained in Examples 1 to 6 each have a relatively wide MWD and a molecular weight dispersion coefficient Mw/Mn of 5 or more; and the sodium hyaluronate samples obtained in Comparative Examples 3 and 4 each have a narrow MWD and a molecular weight dispersion coefficient of 2.5 or less, indicating that an effect of the UV irradiation treatment or hydrogen peroxide treatment alone is not ideal.

Example 9

A tachypiens amebocyte lysate (TAL) reagent method and a Folin-phenol reagent method were used to determine the endotoxin and heteroprotein in each of the sodium hyaluronate samples prepared in Examples 1 to 6, respectively, and results were shown in Table 3.

TABLE 3

Quality test results of sodium hyaluronate

| Example | Endotoxin (EU) | Heteroprotein |
|---|---|---|
| Example 1 | 0.045 | <0.01% |
| Example 2 | 0.031 | <0.01% |
| Example 3 | 0.043 | <0.01% |
| Example 4 | 0.032 | <0.01% |
| Example 5 | 0.026 | <0.01% |
| Example 6 | 0.028 | <0.01% |
| Comparative Example 1 | 0.132 | 0.09 |
| Comparative Example 2 | 0.126 | 0.08 |
| Comparative Example 3 | 0.125 | 0.08 |
| Comparative Example 4 | 0.113 | 0.07 |
| Comparative Example 5 | 0.142 | 0.11 |

It can be seen from the results in Table 3 that the sodium hyaluronate samples obtained by the preparation methods in Examples 1 to 6 each have an endotoxin content of less than 0.01 EU, a protein content of less than 0.01%, an OD value of less than 0.01 at 280 nm, an OD value of less than 0.01 at 260 nm, and high biocompatibility and quality.

Example 10

45 valid volunteer subjects at an age of 20 to 55 were selected, and within 2 d to 3 d before a test, a site to be tested could not be applied with any product including cosmetics and drugs for external use. Before the test, inner sides of two forearms of a subject were collectively cleaned, and 4×4 cm test areas were marked; samples of formulas 1 to 8 (formulas 1 to 6 included 1% of sodium hyaluronate with full MWD in Examples 1 to 6, respectively, formula 7 included 1% of commercially-available sodium hyaluronate with a molecular weight of 1,200,000 Da, and formula 8 included 1% of the sodium hyaluronate in Comparative Example 5; and the remaining components in each of the formulas were 2% of glycerol and 2% of butylene glycol) each were evenly coated randomly on left and right arms at an amount of 3 mg/cm$^2$; and a skin moisture testing instrument was used to test a moisture content of a test skin area before the application of the product and at 30 min, 1 h, 3 h, and 6 h after the application of the product, each test skin area was tested in quintuplicate, and an average was taken. The test for a same subject was completed by a same tester, and all subjects were placed in an indoor space with constant temperature and humidity before and after the test. Increase in skin moisture (%)=(moisture content after application−moisture content before application)/moisture content before application×100%.

TABLE 4

Influence of sodium hyaluronate on skin moisture

|  | 30 min | 1 h | 3 h | 6 h |
| --- | --- | --- | --- | --- |
| Formula 1 | 32.2 ± 1.98 | 31.6 ± 1.45 | 25.0 ± 1.67 | 19.6 ± 1.86 |
| Formula 2 | 33.3 ± 2.12 | 32.3 ± 2.12 | 27.8 ± 2.01 | 20.1 ± 2.02 |
| Formula 3 | 32.3 ± 1.24 | 31.3 ± 21.3 | 28.3 ± 2.08 | 21.3 ± 1.39 |
| Formula 4 | 33.2 ± 1.53 | 32.6 ± 1.85 | 29.6 ± 1.75 | 21.8 ± 0.98 |
| Formula 5 | 32.3 ± 2.12 | 31.4 ± 1.86 | 28.7 ± 1.78 | 21.4 ± 1.57 |
| Formula 6 | 32.2 ± 2.32 | 31.4 ± 2.31 | 29.3 ± 1.82 | 22.6 ± 1.68 |
| Formula 7 | 27.1 ± 1.35 | 25.2 ± 1.62 | 21.4 ± 1.25 | 16.7 ± 1.72 |
| Formula 8 | 30.1 ± 1.30 | 28.1 ± 1.41 | 22.5 ± 1.28 | 17.2 ± 1.56 |

It can be seen from the results in Table 3 that the sodium hyaluronate with full MWD prepared by the present disclosure has better moisturizing performance than the commercially-available sodium hyaluronate products, and can play an excellent moisturizing effect for cosmetics.

Example 11

An inflammatory response induced by interleukin IL-1β in a human immortalized epidermal cell (HaCaT) was taken as a model to verify that the sodium hyaluronate with full MWD prepared by the present disclosure could exhibit an anti-inflammatory effect.

A suspension of the human immortalized epidermal cell (HaCaT) with 5×10$^3$ cells/mL was inoculated in a 96-well plate at 100 μL/well, and 6 replicate wells were set for each group; and the cell was cultivated for 24 h, and a medium including 10 ng/mL interleukin IL-1β and 20 mg/mL sodium hyaluronate with full MWD of the present disclosure (Examples 1 to 6) or control sodium hyaluronate (Comparative Examples 1 to 5) was changed. A cell without IL-1β and sodium hyaluronate was adopted as a normal control group, and a cell with only IL-1β and without sodium hyaluronate was adopted as a model control group. The cell was further cultivated for 24 h, and expression levels of interleukin IL-la and tumor necrosis factor TNF-α were detected by ELISA kits.

TABLE 5

Anti-inflammatory effects of sodium hyaluronate

| Group | IL-la (ng/mL) | TNF-a (ng/mL) |
| --- | --- | --- |
| Normal control group | 43.36 | 1.81 |
| Model control group | 314.23 | 4.35 |
| Example 1 | 102.82 | 2.14 |
| Example 2 | 95.19 | 2.00 |
| Example 3 | 92.17 | 2.07 |
| Example 4 | 97.32 | 1.98 |
| Example 5 | 82.83 | 2.05 |
| Example 6 | 88.67 | 1.92 |
| Comparative Example 1 | 134.73 | 2.93 |

TABLE 5-continued

Anti-inflammatory effects of sodium hyaluronate

| Group | IL-la (ng/mL) | TNF-a (ng/mL) |
| --- | --- | --- |
| Comparative Example 2 | 154.20 | 3.17 |
| Comparative Example 3 | 123.89 | 2.38 |
| Comparative Example 4 | 116.28 | 2.29 |
| Comparative Example 5 | 117.02 | 2.41 |

It can be seen from the data in Table 5 that the sodium hyaluronate samples obtained in the different examples and comparative examples can reduce the expression levels of IL-la and TNF-α in a cell, and all exhibit a specified anti-inflammatory effect; and the sodium hyaluronate with full MWD prepared by the method of the present disclosure has a better anti-inflammatory effect than the ordinary sodium hyaluronate in the comparative examples.

Example 12

Sodium dodecyl sulfate (SDS)-induced skin model damage was taken as a model to verify the anti-cell damage effect and the cell repair effect of sodium hyaluronate with full MWD prepared by the present disclosure.

An EpiSkin skin model was transferred to a 12-well plate and cultivated for 24 h, then the original medium was replaced by a medium including 0.5% (v/v) SDS, and the model was incubated for 2 h; and an equal volume of a medium including 1% (w/v) of the sodium hyaluronate with full MWD of the present disclosure (Examples 1 to 6) or the control sodium hyaluronate (Comparative Examples 1 to 5) was directly added to each well, such that a final concentration of sodium hyaluronate in the medium was 0.5% (w/v). A cell without SDS and sodium hyaluronate was adopted as a normal control group, and a cell with only SDS and without sodium hyaluronate was adopted as a model control group. The skin tissue model was further cultivated for 24 h and then taken out, and an absorbance value at 570 nm was determined with a microplate reader by the MTT method. The histiocyte activity was calculated according to the following formula:

$$\text{histiocyte activity (\%)} = A_{p(t)}/A_n 100\%$$

where $A_{p(t)}$ represents an absorbance value of the positive control group or experimental group and $A_n$ represents an absorbance value of the negative control group. Results were shown in the table below:

TABLE 6

Histiocyte activity of the skin model acted by SDS and sodium hyaluronate

| Group | Histiocyte activity (%) |
| --- | --- |
| Normal control group | 95.11 |
| Model control group | 54.58 |
| Example 1 | 86.34 |
| Example 2 | 88.16 |
| Example 3 | 88.12 |
| Example 4 | 89.57 |
| Example 5 | 89.28 |
| Example 6 | 92.78 |
| Comparative Example 1 | 74.37 |
| Comparative Example 2 | 6819 |
| Comparative Example 3 | 76.34 |
| Comparative Example 4 | 72.28 |
| Comparative Example 5 | 77.56 |

It can be seen from the data in Table 6 that the sodium hyaluronate with full MWD prepared by the present disclosure has a strong inhibitory effect on the SDS-induced EpiSkin skin model damage and can effectively promote the repair of damaged cells; and the sodium hyaluronate with full MWD prepared by the method of the present disclosure has a better cell repair-promoting effect than the ordinary sodium hyaluronate in the comparative examples.

The above are merely preferred embodiments of the present application, and are not intended to limit the present application. Various changes and modifications can be made to the present application by those skilled in the art. Any modifications, equivalent replacements, and improvements made within the spirit and principle of the present application should be included within the protection scope of the claims of the present application.

What is claimed is:

1. A preparation method of sodium hyaluronate with a full molecular weight distribution (MWD), comprising:
    step 1): spraying hydrogen peroxide on a sodium hyaluronate solid raw material, and conducting an ultraviolet (UV) irradiation treatment to obtain a sodium hyaluronate degradation material;
    step 2): dissolving the sodium hyaluronate degradation material in water, and adjusting a pH with a NaOH solution to higher than 7.0 to obtain a sodium hyaluronate alkaline solution;
    step 3): subjecting the sodium hyaluronate alkaline solution to an ultrasonic treatment;
    step 4): preparing the sodium hyaluronate solid raw material into a sodium hyaluronate solution with a concentration of 0.1% to 1% (w/v), and thoroughly mixing the sodium hyaluronate solution with the concentration of 0.1% to 1% (w/v) in an addition proportion of 20% to 60% (v/v) with the sodium hyaluronate alkaline solution obtained after the ultrasonic treatment in step 3); and
    step 5): subjecting a resulting mixed solution to an adsorption treatment with diatomaceous earth and activated carbon, filtering a resulting solution through a nanofiltration membrane for concentration, and drying a resulting concentrate to obtain the sodium hyaluronate with a full MWD, wherein the sodium hyaluronate with the full MWD has a weight-average molecular weight of 2,000 to 1,500,000 and a molecular weight dispersion coefficient Mw/Mn of 5 or more.

2. The preparation method of sodium hyaluronate with the full MWD according to claim 1, wherein in step 1), 50 mL to 100 mL of hydrogen peroxide with a mass concentration of 1% to 5% is sprayed on each kilogram of the sodium hyaluronate solid raw material; and the UV irradiation treatment is conducted for 50 min to 70 min at a dose of 300 µW/cm$^2$ to 1,500 µW/cm$^2$.

3. The preparation method of sodium hyaluronate with the full MWD according to claim 1, wherein the sodium hyaluronate solid raw material has a molecular weight of 1,000,000 to 2,000,000.

4. The preparation method of sodium hyaluronate with the full MWD according to claim 3, wherein the sodium hyaluronate solid raw material is one or more selected from the group consisting of a cosmetic grade sodium hyaluronate, a food grade sodium hyaluronate, and a pharmaceutical grade sodium hyaluronate.

5. The preparation method of sodium hyaluronate with the full MWD according to claim 1, wherein in step 2), a concentration of the sodium hyaluronate degradation material in water is 1% to 10% (w/v); and/or
    the pH is adjusted with the NaOH solution to 10 to 12.

6. The preparation method of sodium hyaluronate with the full MWD according to claim 1, wherein in step 3), the ultrasonic treatment is conducted for 15 min to 180 min at a frequency of 10 kHz to 100 kHz.

7. The preparation method of sodium hyaluronate with the full MWD according to claim 1, wherein in step 5),
    an adsorption treatment with the diatomaceous earth comprises: adding the diatomaceous earth at a mass 0.1% to 1% (w/v) of a mass of the sodium hyaluronate alkaline solution, stirring a first resulting mixture at 45° C. to 80° C. to allow adsorption for 30 min to 60 min, and filtering; and/or
    an adsorption treatment with the activated carbon comprises: adjusting a pH with a dilute acid solution to 6 to 7 to obtain a resulting sodium hyaluronate solution, adding the activated carbon at a mass 0.1% to 1% (w/v) of a mass of the resulting sodium hyaluronate solution, stirring a second resulting mixture at 45° C. to 80° C. to allow adsorption for 30 min to 60 min, and filtering, wherein preferably, the dilute acid solution is one or more selected from the group consisting of a dilute hydrochloric acid solution, a dilute sulfuric acid solution, a dilute acetic acid solution, and a dilute hypochlorous acid solution.

8. The preparation method of sodium hyaluronate with the full MWD according to claim 1, wherein in step 5), the nanofiltration membrane has a molecular weight cut-off (MWCO) of 200 Da to 300 Da, and the filtering is conducted at a pressure of 15 bar to 30 bar and a temperature of 30° C. to 50° C.

9. A method of preparing a drug or a cosmetic comprising a step of adding the sodium hyaluronate with a full MWD prepared by the preparation method according to claim 1 to a moisturizer, a lubricant, or an anti-inflammatory agent.

10. The method according to claim 9, wherein in step 1), 50 mL to 100 mL of hydrogen peroxide with a mass concentration of 1% to 5% is sprayed on each kilogram of the sodium hyaluronate solid raw material; and the UV irradiation treatment is conducted for 50 min to 70 min at a dose of 300 µW/cm$^2$ to 1,500 µW/cm$^2$.

11. The method according to claim 9, wherein the sodium hyaluronate solid raw material has a molecular weight of 1,000,000 to 2,000,000.

12. The method according to claim 11, wherein the sodium hyaluronate solid raw material is one or more selected from the group consisting of a cosmetic grade sodium hyaluronate, a food grade sodium hyaluronate, and a pharmaceutical grade sodium hyaluronate.

13. The preparation method of sodium hyaluronate with the full MWD according to claim 1, wherein the sodium hyaluronate with the full MWD has an endotoxin content of less than 0.01 EU and a protein content of less than 0.01%; and an OD value of less than 0.01 at 280 nm and an OD value of less than 0.01 at 260 nm.

* * * * *